(12) United States Patent
Crosby et al.

(10) Patent No.: US 7,077,857 B1
(45) Date of Patent: Jul. 18, 2006

(54) PULSE CAM

(75) Inventors: Charles Crosby, Orlando, FL (US); W. Paul Sayre, Orlando, FL (US); Dick Downes, Orlando, FL (US)

(73) Assignee: Crosby Advanced Medical Systems, Inc., Winter Park, FL (US)

( * ) Notice: Subject to any disclaimer, the term of this patent is extended or adjusted under 35 U.S.C. 154(b) by 0 days.

(21) Appl. No.: 10/084,008

(22) Filed: Feb. 27, 2002

(51) Int. Cl.
*A61B 18/18* (2006.01)
(52) U.S. Cl. ........................................ 607/88
(58) Field of Classification Search ............... 606/1, 606/3, 10–13; 607/88–94
See application file for complete search history.

(56) References Cited

U.S. PATENT DOCUMENTS

| | | | | |
|---|---|---|---|---|
| 1,510,080 | A * | 9/1924 | Murphy | 607/90 |
| 2,306,909 | A | 12/1942 | Sykes | 171/327 |
| 3,371,234 | A | 2/1968 | Cady | 310/9.5 |
| 4,708,127 | A | 11/1987 | Abdelghani | 128/24 |
| 4,869,666 | A * | 9/1989 | Talass | 433/20 |
| 5,158,070 | A | 10/1992 | Dory | 128/240 |
| 5,230,334 | A | 7/1993 | Klopotek | 128/399 |
| 5,989,202 | A | 11/1999 | Noda et al. | 601/2 |
| 6,113,559 | A | 9/2000 | Klopotek | 601/3 |
| 6,217,530 | B1 | 4/2001 | Martin et al. | 601/2 |
| 6,238,421 | B1 | 5/2001 | Gunther et al. | 607/13 |

OTHER PUBLICATIONS

*Liss Body Stimulator*, Professional Instrument Manual, SBL 502-B, Oct. 26, 1994, pp. 1-8.
*TENSCAM Profession Manual*, Charles Crosby, Sep. 15, 2001, pp. 1-8.

* cited by examiner

*Primary Examiner*—David M. Shay
(74) *Attorney, Agent, or Firm*—Brian S. Steinberger; Law Offices of Brian S. Steinberger, P.A.

(57) ABSTRACT

Battery powered and wall plug powered handheld therapy devices for treating a variety of ailments such as inflammations, nerve problems, joint pain, muscle pain, as well as gall bladder type problems. The device can have a multi-faced shaped emitting main crystal with side crystals that can be used with a flashing strobe light source to generate variable frequency pulses toward the effected body part to be treated. Alternatively, or additionally, the device can use an electromagnetic type generator to generate fixed frequency signals toward an effected body area to be treated. Up to approximately six small crystals or more can be positioned to a base portion of the emitting crystal on each of the six faces of the emitting crystal. The side crystals can be used as antennas to receive ambient energy in order to be focused by the main crystal. Hand grips or a floor based stand can be used to elevate the device up to approximately 18 inches above the patient. Effective treatment with the device has been achieved within approximately 2 minutes of use.

12 Claims, 3 Drawing Sheets

PULSE CAM

This invention relates to medical devices, and in particular to methods and apparatus for generating emissions and focusing the energy and emissions through a light pulse powered handheld tool unit or an electromagnetic powered tool or a combination tool for therapeutic treatments.

BACKGROUND AND PRIOR ART

Ultrasound and vibratory type emitting devices have been used for medical therapeutic applications over the years. Various types of therapeutic devices have been proposed that apply ultrasonic oscillations and vibrations directly to an affected body part so as to relax muscles, quicken blood flow circulation, enhance healing of the skin, etc. See For example, U.S. Pat. No. 4,708,127 to Abdelghami; U.S. Pat. Nos. 5,230,334 and 6,113,559 to Klopotek; and U.S. Pat. No. 5,989,202 to Noda et al.

However, these devices and systems have practical type limitations. For example, most of these devices are limited to direct contact of a portion of the device itself against the skin of the patient. As a result, the field of application is generally restricted to the areas directly beneath the skin contact point. The body contacting requirement does not allow these devices to easy slide over and across one's skin to different areas to be treated. Thus, moving these devices to other body areas usually requires that the device be physically raised, moved and lowered again to the area to be treated.

Furthermore, these devices are generally limited to using acoustical type vibratory signal emissions from a single generator type unit such as an electromagnetic generator, and does not use other energy sources, nor applies other energy emissions for treatments. Still furthermore, the single generators are generally limited to generating only fixed frequency outputs.

The subject inventor has previously sold a handheld tool entitled: Tens Cam having a single fixed frequency generating crystal that solely relied on an electromagnetic induction coil to drive the single crystal. A fixed frequency of approximately 8 Hertz was generated by an electromagnetic source in a narrow beam having a diameter of approximately 1 to approximately 2 millimeters. The delay time for therapeutic effects of the Tens Cam unit was approximately two to approximately four (4) minutes to generate therapeutic effects on the patient which became difficult to do over continuous treatments that required the operator to physically hold the unit which weighed almost one pound, above the patient being treated. In addition other problems existed with this unit. Operator fatigue was an inherent result of using this unit.

The Tens Cam unit required an operator to physically hold the unit above a patient throughout the treatment process so that the operator received direct vibratory effects from physically holding the unit. The combination of constantly holding the weight of the unit and the direct vibratory effects, along with the operator being constantly within the generation field of the unit created side effects such as but not limited to fatigue and malaise for the operator. Operators repeatedly using the Tens Cam have complained of side effects of median nerve paraethias, which is a numbness and tingling effect to their hands and fingers.

Additional problems with other electromagnetic and with vibratory units is that all these units can be known to give off heat which has caused tissue damage. Furthermore, theses prior art type units have limitations as to the tissue penetration being achieved, since the tissue penetration depth is limited by the mechanical nature of the vibrations.

None of these devices described above takes in additional energy to aid in the therapy treatment. Thus, these prior art devices are limited to mechanical devices and do not incorporate other approaches with their use. Furthermore, using strictly handheld supported devices can potentially injure the patients themselves, if the operator directly contacts the patients with the devices.

SUMMARY OF THE INVENTION

A primary objective of the invention is to provide a tool for therapy treatments that does not have to be in contact with the skin surface of a patient, that does not have the tissue depth penetration limitations of electromagnetic sources and vibratory devices.

A secondary objective of the invention is to provide a tool for therapy treatments that can combine an energy generating source along with an ambient receiver to effect medical treatment effects at resonating emissions of approximately 7 to approximately 8 Hertz.

A third objective of the invention to provide a tool for therapy treatments that can alternate between a fixed frequency output and a variable frequency range of emissions to include the resonant frequency of the patient being treated of between approximately 4 to approximately 15 Hertz.

A fourth objective of the invention is to provide a tool for therapy treatments that can be handheld above a body part to be treated.

A fifth objective of the invention is to provide a tool for therapy treatments that can be mounted on a stand which supports the tool above the body part to be treated.

A sixth objective of the invention is to provide a tool for therapy treatments that reduces and eliminates patient injury risks, and allows for most any body tissue to be easily reached and treated by the tool.

A seventh objective of the invention is to provide a tool for therapy treatments that reduces and potentially eliminates fatigue and malaise injuries to the tool operator or previously known devices.

An eighth objective of the invention is to provide a tool for therapy treatments that can achieve therapeutic results within approximately 2 (two) minutes as compared up to 4 (four) minutes that was required with previous tools.

Three embodiment applications for using the invention are disclosed. A first embodiment uses a flash lamp generator that generates with side crystals and a main crystal with lens, a variable 4 to approximately 15 Hertz output in a approximately 5 to approximately 6 diameter beam positioned up to approximately 18 inches over the body part being treated. Treatment effectiveness has occurred within approximately 2 minutes of being treated.

A second embodiment uses an electromagnetic generator with the main crystal and side crystals and output lens to generate a fixed output of approximately 7 to approximately 8 Hertz. A third embodiment combines the first and second embodiments.

The novel tool can be powered by a wall plug, batteries, combinations thereof, and the like. A novel stand can support the tool at fixed distances over the patient being treated. If used by hand, a protective foil can be used inside of the tool to eliminate any of the tools output from reaching the operator.

Further objects and advantages of this invention will be apparent from the following detailed description of a presently preferred embodiment which is illustrated schematically in the accompanying drawings.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

Figure 1:
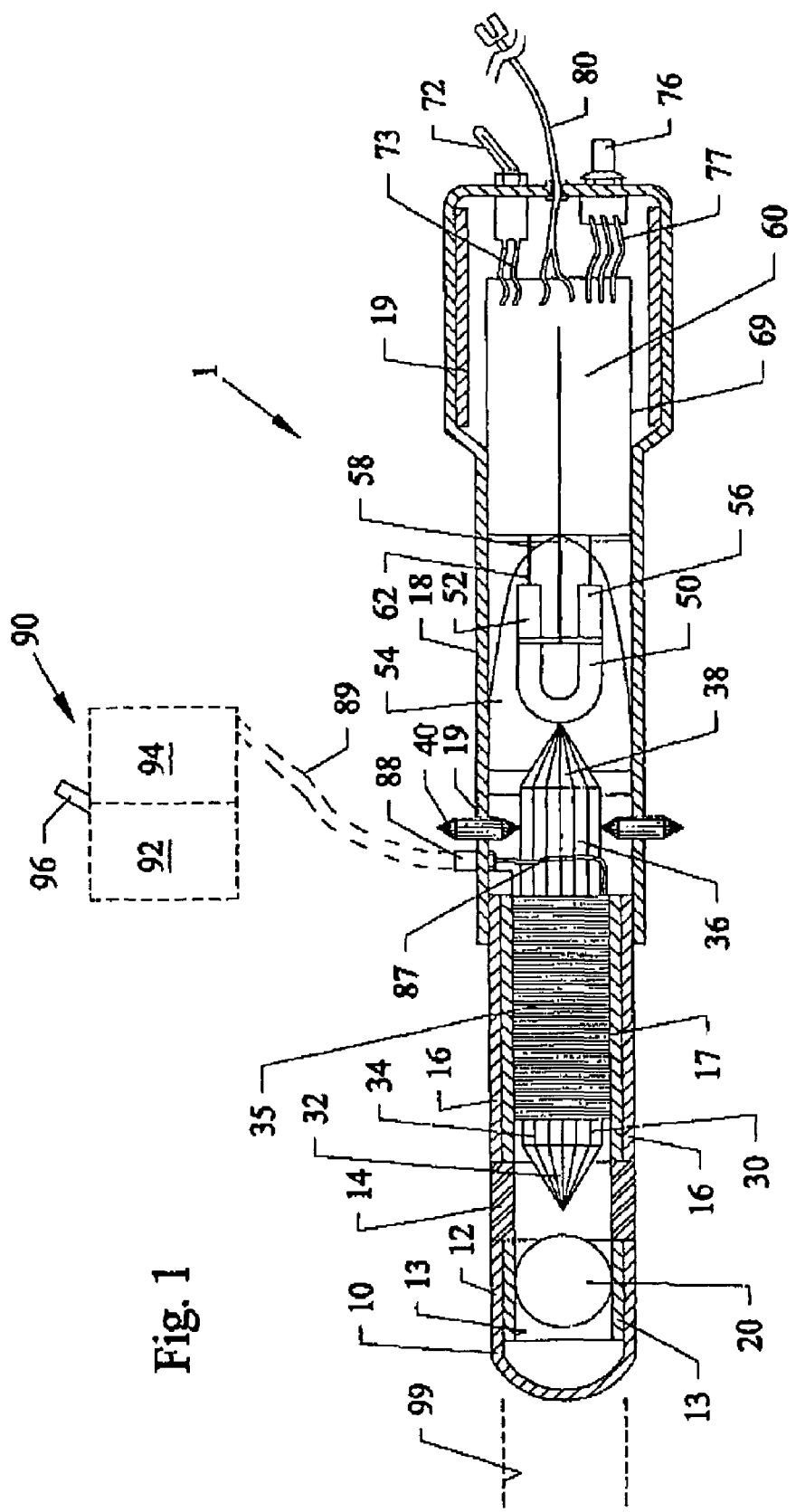
FIG. 1 is a cross-sectional view of a novel pulse cam device invention.

FIG. 1 is a cross-sectional view of a novel pulse cam device invention 1. The device 1 can include a lens emitting end cap 10 and sleeve 12 which can be formed from a flexible transparent plastic, and the like. Within sleeve 12, can be a secondary cylindrical sleeve also formed from a plastic transparent material that can be used to support a divergent lens 20 as a combined diffuser and amplifier, such as but limited to a crystal sphere formed from silicon dioxide, quartz, and the like. In the preferred embodiment, the sphere used as lens 20 can have a diameter of approximately 4.5 cm.

The base of the cap and sleeve 12 can abut against a cylindrical plastic type clear sleeve window that allows one to view the flashing of the strobing crystal 30 which will be described in detail later. A middle cylindrical sleeve 16 is joined to the window sleeve 12, and a rear cylindrical sleeve housing 18 such as a PVC pipe, attaches to the middle cylindrical sleeve 16, which expands to a closed cap end 19.

A press joint 13 within sleeve 12 allows for a tight machine fit between components to fixably support the lens 20. A second press joint 17 can be located within middle cylindrical sleeve 16 for supporting the main crystal 30 therebetween.

Main crystal 30 can be an elongated multi-flat sided crystal with tapered multi-flat sided ends having pointed end tips, and can be chosen from materials such as a Lemurian Crystal, a quartz crystal, silicon dioxide, and the like. Main crystal 30 can be an elongated crystal with multi-faceted (up to approximately six sided or more flat faces) front tip end 32, cylindrical multi-faceted (up to approximately six sided or more flat faces) middle portion 34, 36 and multi-faceted (up to approximately six sided or more flat faces) rear tip end 38. Main crystal 30 can have dimensions of approximately 18 cm long by approximately 3 cm wide with ends 32, 38 tapering down to sharp tips with the ends 32, 38 having a length of approximately 2 cm.

Wrapped about a mid portion of main crystal 30 between front end 32 and rear end 36 can be an energy transfer coil 35 such as an electromagnet coil (such as but not limited to a copper wire coil).

Referring again to FIG. 1, and protruding from the rear middle portion 36 of main crystal 30 can be multi-faceted (up to approximately six sided or more flat faces) crystals 40, each protruding in a direction perpendicular to each of the flat faces on the sides of the rear tip end 38. Each of the side crystals 40 can be formed from materials such as a Lemurian Crystal, a quartz crystal, silicon dioxide, and the like. Side crystals 40 can each pass through side openings 19 in the housing sleeve 18 of the device 1. Side crystals 40 can have dimensions of approximately 2.5 cm long by approximately 1 cm wide. Side crystals 40 can be used as antennae to pickup ambient energy fields about the tool 1. Additionally, when used with the flash lamp 50/60, the side crystals will emit some flashing light, and their location can be used so that any operators of the tool position their hands to the right of the crystals 40 so that both the reflector 58 and shield 69 (both to be described later) help protect the operator from the tool 1.

Within rear housing sleeve 18 of tool 1 can be a U-shaped flash tube 50 with control board 60 such as but not limited to a Velman Kit having a Strobro scope K5300 power plug and flash lamp. Additionally, a protective material 69 such as a foil shield, and the like, can be wrapped about these components to limit exposure to any operators. Behind flash tube 50 can be a curved reflector 58 having an interior concave mirrored face. Curved reflector 58 can be positioned about arms 52, 56 of flash tube 50, and curved portion 54 can abut against rear tip end 38 of main crystal 30.

The arms 52, 56 of flash tube 50 can be connected to a power supply 80 by electrical feed lines 62, 66 to the flash tube circuit control board 60. An on/off toggle type switch 72 can be connected by line 73 to the control board 60, to turn power on and off to the device 1. A variable control 76 such as a rotatable rheostat type control, connected by feed line 77 to control board 60, can control the flashing frequency of flash tube 50, which can flash across a frequency range of approximately 4 to approximately 15 Hertz.

Power to the tool 1 using the flash lamp 50/60 can be by an AC (alternating Current) 120 volt wall plug source 80.

Three different operational modes of using the tool 1 will now be described. A first operational mode uses just the flash lamp 50/60. A second mode uses only the electromagnetic coil 35 and exterior adapter 90. A third operational mode can combine the first and second modes.

In the operational mode using the flash lamp 50/60, the electromagnetic coil 35 and exterior adapter 90 are not used. Here the flash lamp 50/60 generates pulsing light to pass into the main crystal 30 which can be amplified by side antenna crystals 40, and further diffused and amplified by divergent lens 20 into the air and into a patient spaced away from the tool 1. The output beam 99 being generated can have a diameter of approximately 5 to approximately 6 cm and can be emitted in the range of approximately 4 to approximately 15 Hertz by varying the variable rheostat controller 76. The output beam 99 in tool 1 is substantially larger than that of the prior art Tens Cam described in the background section of the invention which was limited to a narrow beam of approximately 1 to approximately 2 millimeters.

In the second operational mode, a Tens Cam adapter such as that used in the prior art previously described can be used with tool 1, which can include an exterior pulse generator pack 90 can be used with tool 1. Exterior generator, can be connected by leads 89 that are attachable to a removable exterior connector plug 88 through interior leads 87 to electromagnetic coil 35 wrapped about main crystal 30. The exterior pulse generator 90 that can be used can be a Liss Body Stimulator Bipolar Model No. SBL-502-B. The generator 90 can include a battery power pack 92 having a 9 volt battery source, that powers a waveform signal generator component 94. The Tens Cam adapter embodiment contains an approximately 15,000 Hertz square wave carrier which can be rectified, varying from zero to a maximum of approximately 4 mill amperes. A first modulating signal of approximately 15 Hertz can provide an "on" time of approximately 50 milliseconds and an "off" time of approximately 16.7 milliseconds. A second modulating signal of approximately 500 Hertz changes the "on" time series of approximately 15,000 Hertz carrier pulses (approximately 750 pulses in approximately 50 milliseconds) into approximately 25 smaller bursts of approximately 15 pulses each of the 15,000 Hertz carrier signal (approximately 375 pulses in the same 50 milliseconds). The signals pass through the main crystal 30 by the electromagnetic coils 35 wrapped about crystal 30. With the adapter version 90 turned on by toggle type switch 92, a fixed emission of approximately 7.75 Hertz (approximately 8 Hertz) can be emitted from tool 1.

In the embodiment mode limited to using the electromagnetic adapter, square waves pass through electromagnetic coils 35 and into main crystal 30, the latter of which is amplified by side crystals 40. Signals passing from the tip end 32 of main crystal 30 are further amplified and diffused by lens 20 and pass into the air in a beam 99 having a diameter of approximately 5 to approximately 6 cm. As previously noted this diameter is substantially larger than the Tens Cam prior art device previously described in the background section of the invention. With the electromagnetic adapter 90, tool 1 can emit a fixed output emission of approximately 8 Hertz.

A third operational mode can combine both the first mode using the flash lamp 50/60 source and the second mode using the electromagnetic generator source 90.

Figure 2:
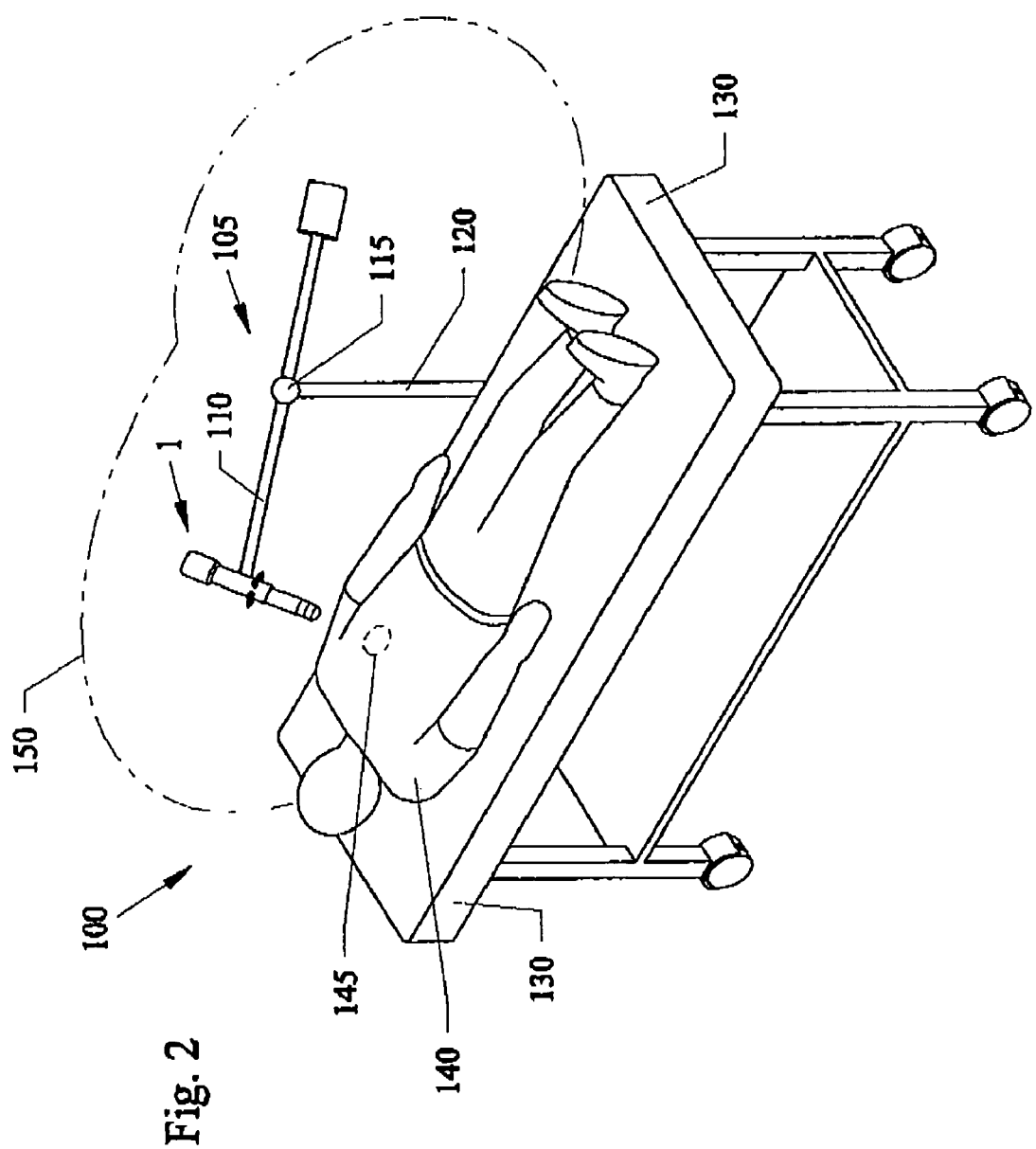
FIG. 2 shows the invention of FIG. 1 on a floor stand ready to be used before treatment.

FIG. 2 shows the invention device 1 of FIG. 1 on a floor stand 110/120 ready to be used before treatment. A floor stand 105 includes a floor supported vertical stand leg 120 with a boom arm 110 pivotally mounted on the stand leg 120, with the novel device 1 mounted to the boom arm 110. A patient 140 can be placed on a medical treatment table 130, such as being placed on their back. The flashing crystal 30 is visible through the clear window 14 (as shown in FIG. 1) in the device 1.

A health practitioner can position the arm 110 to a selected position over the patient 140 up to approximately 18 inches over the body part 145 being treated. The effected body part can be a gall bladder, joint pain, back pain, tissue damage, bone ligaments, organs, and the like. Additionally, the novel tool can have therapeutic treatments for patients suffering from chronic type pain, joint pains, back pains, neck pains, hip pains, and shoulder pains.

Testing of the novel tool 1 using the three operational modes previously described has determined that treatment has been effective with various physically painful ailment areas such as those listed in Table 1 within time frames of up to approximately 2 minutes which is substantially less than the approximately 2 to approximately 4 minutes that was needed with the prior art Tens Cam unit. Ultrasound studies taken from various patients have shown that less inflammation exists about the treated body areas. These painful ailments were present prior to Tens Cam treatment. This is objective evidence to support subjective improvement. Thus, the tool 1 shows anti-inflammatory results in the areas listed in Table 1 below.

TABLE 1

| AILMENTS Column 1 List | AILMENTS Column 2 List |
| --- | --- |
| Ankle Sprain | Headache |
| Tennis Elbow | Earache |

TABLE 1-continued

| AILMENTS Column 1 List | AILMENTS Column 2 List |
| --- | --- |
| Torn Meniscus | Sinusitis |
| Back Pain | Burns |
| Nerve Root | Wounds |
| Bursitis | Abrasions |
| Neck Pain | GERD |
| Hernia | TMJ |
| Gallbladder | Morton's Neuroma |
| Foot Pain | Arthritis |
| Scars | Sore Throat |
|  | Shingles |

Figure 3:
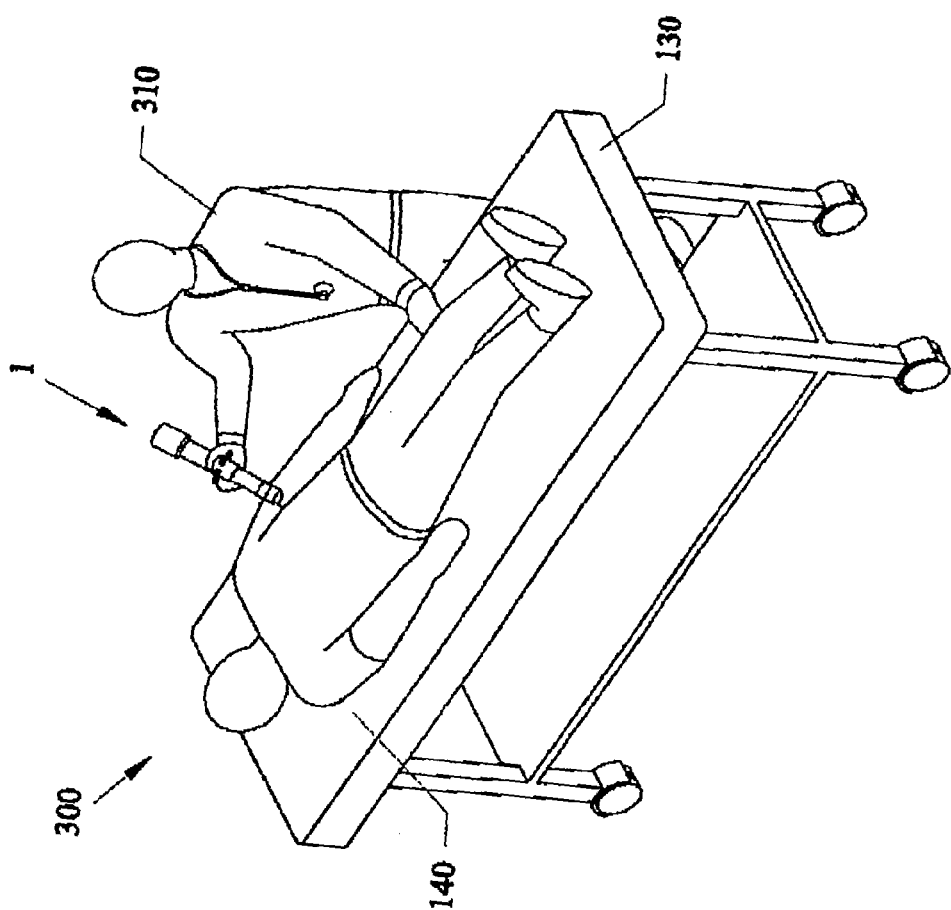
FIG. 3 shows the invention of FIG. 1 being handled by a healthcare practitioner.

FIG. 3 shows an application 300 the invention tool 1 of FIG. 1 being handled by a healthcare practitioner/operator 310. Operator 310 can physically hold tool 1 a selected position over the patient 140 up to approximately 18 inches over the body part 145 (FIG. 2) being treated, and has been similarly tested to show positive healing effects within approximately 2 minutes of being used which is substantially less than the approximately 2 to approximately 4 minutes that was needed with the prior art Tens Cam unit described in the background section of the invention. Referring to FIGS. 1 and 3, the protective shield 69 such as a foil wrap along with the reflector 58 having interior facing mirror surface that can be used inside of the tool helps eliminate any of fatigue and malaise results that have occurred to operators handling prior art tools.

Although one of the embodiments is described using a battery and another embodiment uses a wall plug power source, either or both embodiments can use battery and wall plug power supplies.

Additionally, although one embodiment has been described as using a fixed frequency output, and one embodiment using a variable emission output, either or both embodiments can generate fixed frequency outputs and/or variable frequency outputs.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A medical treatment device comprising:
   a main longitudinal solid crystal having a base portion and an emitting tip portion;
   a crystal sphere next to the emitting tip portion of the main longitudinal body; and
   a power source for generating a resonating frequency in the main crystal through the emitting tip portion of the main longitudinal crystal into an output signal which is amplified and diffused by the crystal sphere toward an effected body part for treatment for up to approximately 2 (two) minutes; and
   side crystals arranged about side portions of the main longitudinal crystal between the base portion and the tip portion, the side crystals having axes being perpendicular to a longitudinal axes of the main longitudinal crystal, the side crystals being used as antennae to receive ambient energy fields about the device.

2. A medical treatment device comprising:
   a main longitudinal crystal having a base portion and an emitting tip portion;

side crystals arranged about side portions of the main longitudinal crystal between the base portion and the tip portion, the side crystals having axes being perpendicular to a longitudinal axes of the main longitudinal crystal, the side crystals being used as antennae to receive ambient energy fields about the device;

means for generating a resonating frequency in the main crystal which is focused by the emitting tip portion of the crystal toward an effected body part for treatment for up to approximately 2 (two) minutes; and a power supply for supplying power to the generating means; and a crystal sphere lens adjacent to the emitting tip portion of the main longitudinal crystal for diffusing and amplifying signals from the emitting tip portion of the main crystal, the crystal sphere lens forming a beam having a diameter of approximately 5 cm to approximately 6 cm.

3. The device of claim 1, wherein the main crystal includes:

up to approximately six (6) multi-faces.

4. The device of claim 1, further comprising:

a handheld grip for positioning the device up to approximately 18 inches above the effected body part being treated.

5. The device of claim 1, further comprising:

a floor supported stand for supporting the device up to approximately 18 inches above the effected body part being treated.

6. The device of claim 1, wherein the generating means includes: an electromagnetic driver.

7. The device of claim 1, wherein the generating means includes: a flash lamp source.

8. The device of claim 1, wherein the resonating frequency includes: a variable range of approximately 4 Hertz to approximately 15 Hertz.

9. The device of claim 1, further comprising:

means for alternating between a fixed resonating frequency, and a variable resonating frequency.

10. The device of claim 1, wherein the generating means includes:

an electromagnetic driver wrapped about the main longitudinal crystal; and a flashlamp generator source adjacent to the base portion of the main longitudinal crystal.

11. The device of claim 1, wherein the resonating frequency includes: a fixed frequency of approximately 7 to approximately 8 Hertz.

12. The medical treatment device of claim 11, wherein the power source includes both:

an electromagnetic driver wrapped about the main longitudinal crystal; and a flashlamp generator source adjacent to the base portion of the main longitudinal crystal.

* * * * *